United States Patent [19]

Green

[11] Patent Number: 4,530,453

[45] Date of Patent: Jul. 23, 1985

[54] SURGICAL FASTENER APPLYING APPARATUS

[75] Inventor: David T. Green, Norwalk, Conn.

[73] Assignee: United States Surgical Corporation, Norwalk, Conn.

[21] Appl. No.: 538,830

[22] Filed: Oct. 4, 1983

[51] Int. Cl.³ .............................................. A61B 17/04
[52] U.S. Cl. ................................. 227/19; 128/334 R; 227/DIG. 1; 227/135
[58] Field of Search ....... 128/334 R; 227/19, DIG. 1, 227/135

[56] References Cited

U.S. PATENT DOCUMENTS

| | | | |
|---|---|---|---|
| 2,853,074 | 9/1958 | Olson | 128/322 |
| 2,891,250 | 6/1959 | Hirata | 1/50 |
| 3,275,211 | 9/1966 | Hirsch et al. | 227/19 |
| 4,354,628 | 10/1982 | Green | 227/19 |
| 4,383,634 | 5/1983 | Green | 227/19 |

FOREIGN PATENT DOCUMENTS 1835500  4/1961  Fed. Rep. of Germany.

*Primary Examiner*—Paul A. Bell
*Attorney, Agent, or Firm*—Robert R. Jackson; John E. Nathan

[57] ABSTRACT

In a surgical fastener applying instrument of the type in which the tissue is first clamped by operation of a lever mechanism, a releasable latch is included in the lever mechanism for releasably holding the tissue clamping elements at an intermediate latching position. In this position, the tissue to be fastened is enclosed but not fully clamped by the instrument so that the position of the instrument relative to the tissue can be adjusted without reopening the instrument.

13 Claims, 9 Drawing Figures

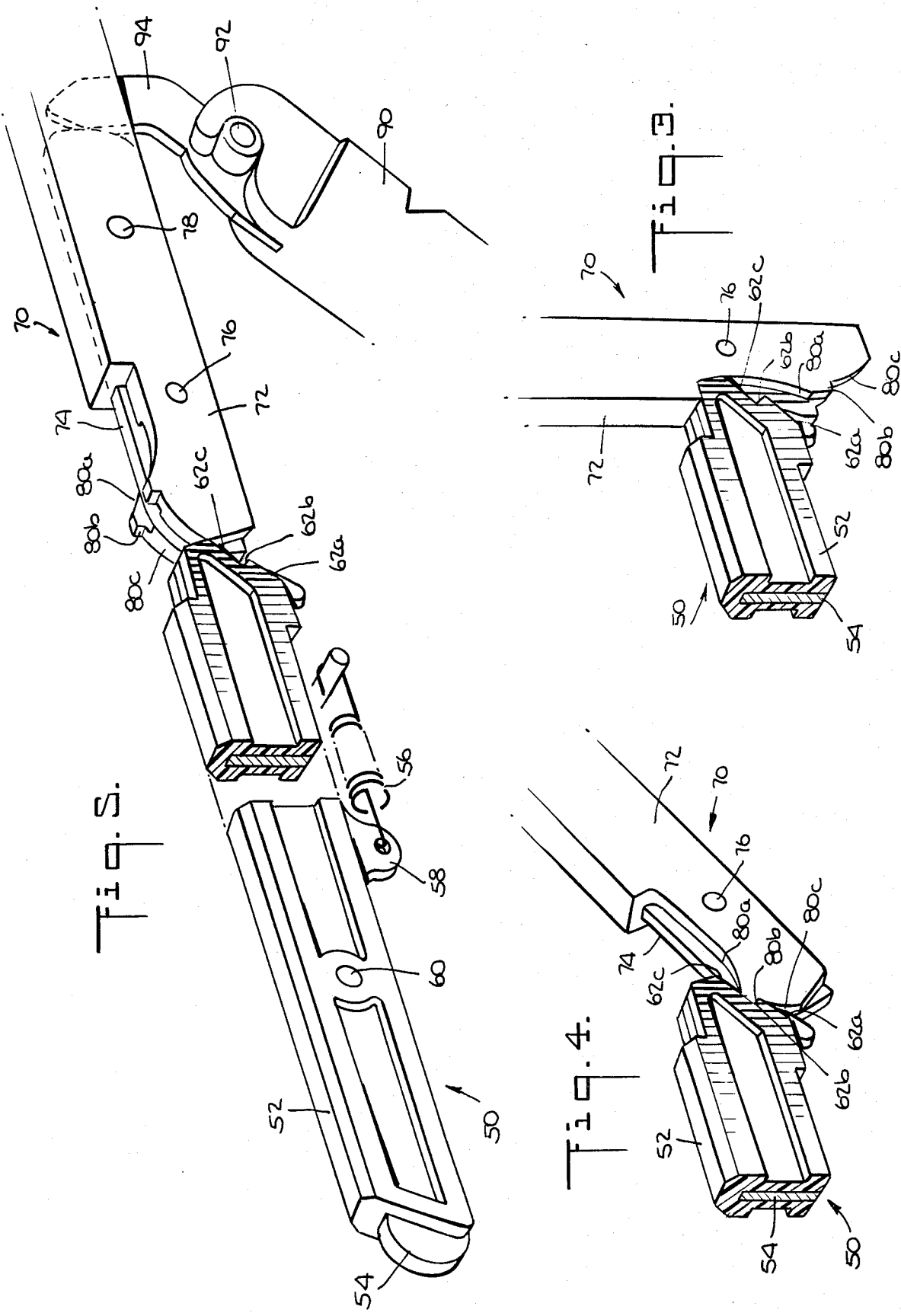

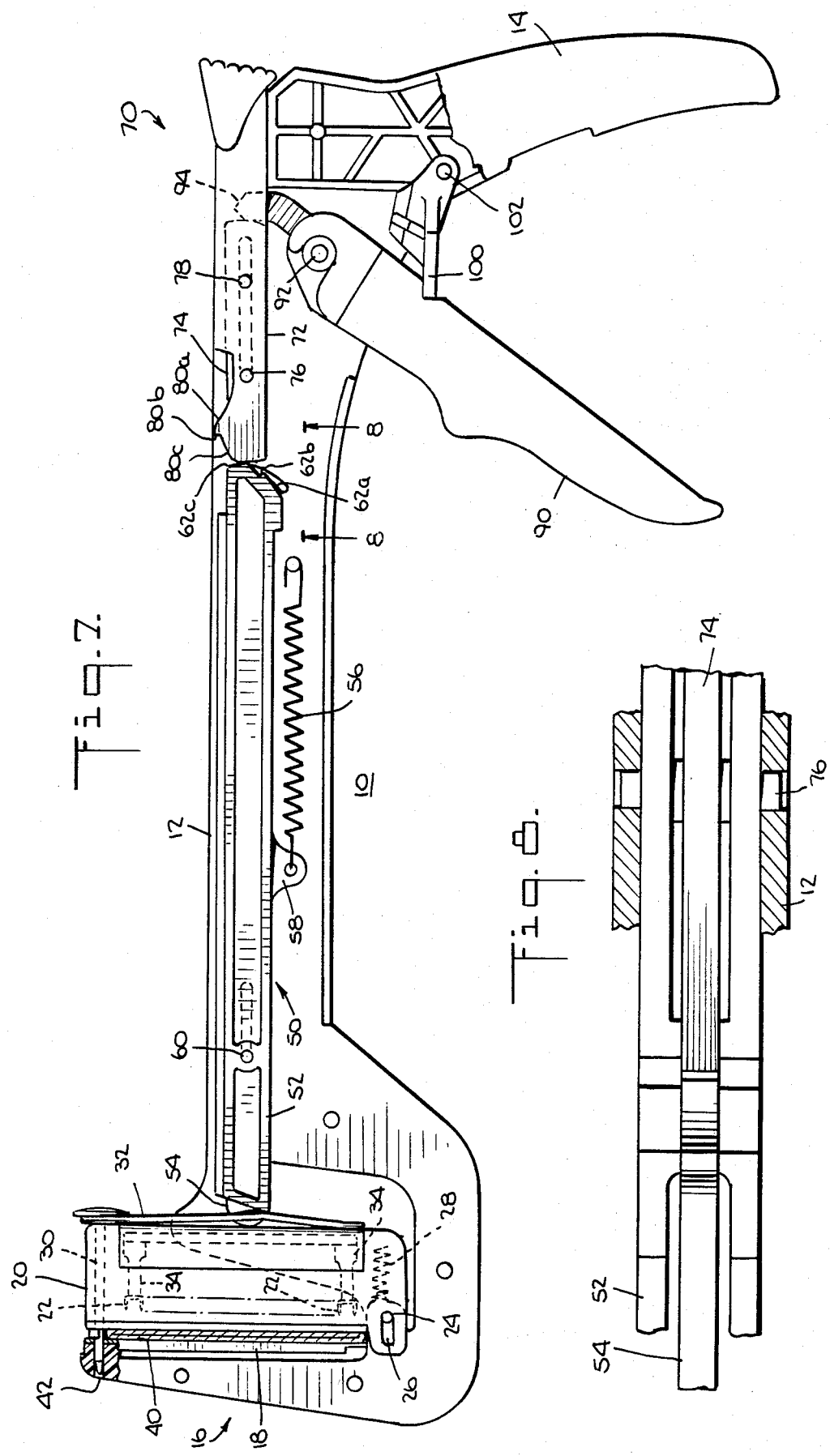

SURGICAL FASTENER APPLYING APPARATUS

BACKGROUND OF THE INVENTION

This invention relates to surgical fastener applying apparatus, and more particularly to surgical fastener applying apparatus in which the tissue to be fastened is first clamped in the apparatus and then fastened by application of the fasteners.

Various devices have been developed for applying surgical fasteners in lieu of conventional sutures. Some of these devices apply metal staples; others apply two-part fasteners of resinous materials. The term "surgical fasteners" is used herein as a generic term for all such fasteners.

Many surgical fastener applying devices, especially those intended for fastening internal body tissue, are designed to clamp the tissue before applying the surgical fasteners to it. The known devices of this kind take several forms. Hirsch et al. U.S. Pat. No. 3,275,211 shows a device in which a surgical staple holding assembly reciprocates linearly relative to an anvil in response to rotation of a control knob. After tissue has been clamped between the anvil and the staple holding assembly, a plurality of metal surgical staples are driven simultaneously by operation of a pivoting handle.

Green U.S. Pat. Nos. 4,354,628 and 4,383,634 show other devices which accomplish a similar result in a different way. In the Green devices, the staple holding assemblies are pivotally mounted relative to the anvil (although limited relative linear translation of these elements may also be possible in these devices). Pivoting levers are used to pivot the staple holding assembly toward the anvil in order to clamp the tissue between these elements. After the tissue has been clamped, a pivoting handle is operated to simultaneously drive a plurality of metal staples through the tissue.

Green U.S. Pat. No. 4,383,634 (FIG. 14) shows that the use of levers to control the tissue clamping function is not limited to devices in which the fastener holding assembly and the anvil are pivotally related. This principle can also be applied to devices in which the fastener holding assembly translates linearly relative to the anvil as in the Hirsch et al. device.

Devices of the type shown by Hirsch et al., in which a knob is used for controlling the position of the staple holding assembly, have the characteristic that the spacing between the staple holding assembly and the anvil is adjustable by the operator. On the other hand, operation of devices of the type shown by Green, in which levers are used to close the device on the tissue, may be faster.

Because the spacing between the staple holding assembly and the anvil in devices of the type shown by Green is not adjustable, it is generally not possible to adjust the location of the apparatus relative to the tissue after the tissue has been clamped. Of course, it is usually possible to reopen the instrument and reposition it if the original position is not satisfactory. But it would be desirable to have the ability to adjust the position of the apparatus relative to the tissue without having to completely reopen the instrument.

It is therefore an object of this invention to improve surgical fastener applying apparatus of the type in which levers are used to operate the elements which clamp the tissue prior to application of the surgical fasteners.

It is a more particular object of this invention to provide surgical fastener applying apparatus having levers for operating the elements which clamp the tissue prior to fastening and having an intermediate latching position in which the instrument is partly closed on the tissue but the tissue is not clamped so that the position of the instrument relative to the tissue can be adjusted without reopening the instrument.

SUMMARY OF THE INVENTION

These and other objects of the invention are accomplished in accordance with the principles of the invention by providing releasable latching elements on the lever members which operate the tissue clamping elements in surgical fastener applying apparatus having lever-actuated tissue clamping. The latching elements releasably hold the tissue clamping elements in a partially closed position in which the tissue is not yet fully clamped. Accordingly, the position of the instrument relative to the tissue can be adjusted if desired. When the position of the instrument is completely satisfactory, the instrument is operated further to clamp the tissue and apply the surgical fasteners.

Further features of the invention, its nature and various advantages will be more apparent from the accompanying drawing and the following detailed description of the invention.

BRIEF DESCRIPTION OF THE DRAWING

FIG. 3 is a detailed perspective view of a portion of the apparatus of FIG. 2.

FIG. 4 is a view similar to FIG. 3 showing the apparatus at a different stage in its operating cycle.

FIG. 5 is a view similar to FIGS. 3 and 4 (with some additional elements visible) showing the apparatus at yet another stage in its operating cycle.

FIG. 7 is a view similar to FIG. 6 showing the apparatus in the operating condition depicted in FIG. 5.

FIG. 8 is a fragmentary sectional view taken along the line 8—8 in FIG. 7.

DETAILED DESCRIPTION OF THE INVENTION

Figure 1:
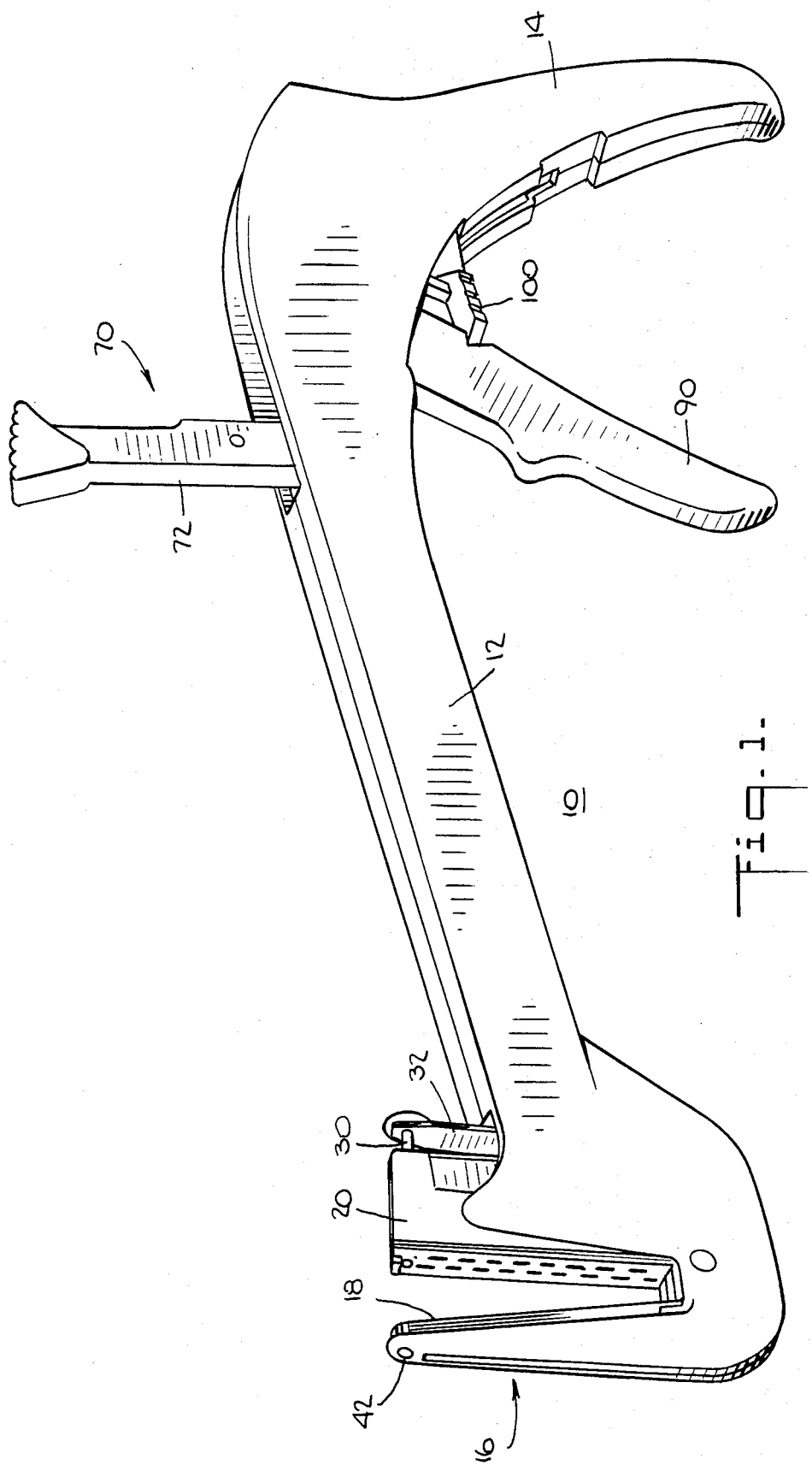
FIG. 1 is a perspective view of an illustrative embodiment of surgical fastener applying apparatus constructed in accordance with the principles of the invention.

Illustrative surgical fastener applying instrument 10 includes an elongated shaft 12 having a fixed handle 14 connected to its proximal end and a surgical fastener applying assembly 16 connected to its distal end. Fastener applying assembly 16 has two major components: (1) anvil assembly or member 18, which is rigidly connected to shaft 12; and (2) surgical fastener holding assembly 20, which is mounted for both pivotal and limited linear translational motion relative to anvil member 18. Surgical fastener holding assembly 20 initially contains a plurality of U-shaped metal surgical staples 22 (FIG. 7) arranged in two parallel rows. If desired, two-part plastic surgical fasteners of the type shown, for example, in Noiles U.S. Pat. No. 4,060,089 can be substituted for metal staples 22.

Figure 2:
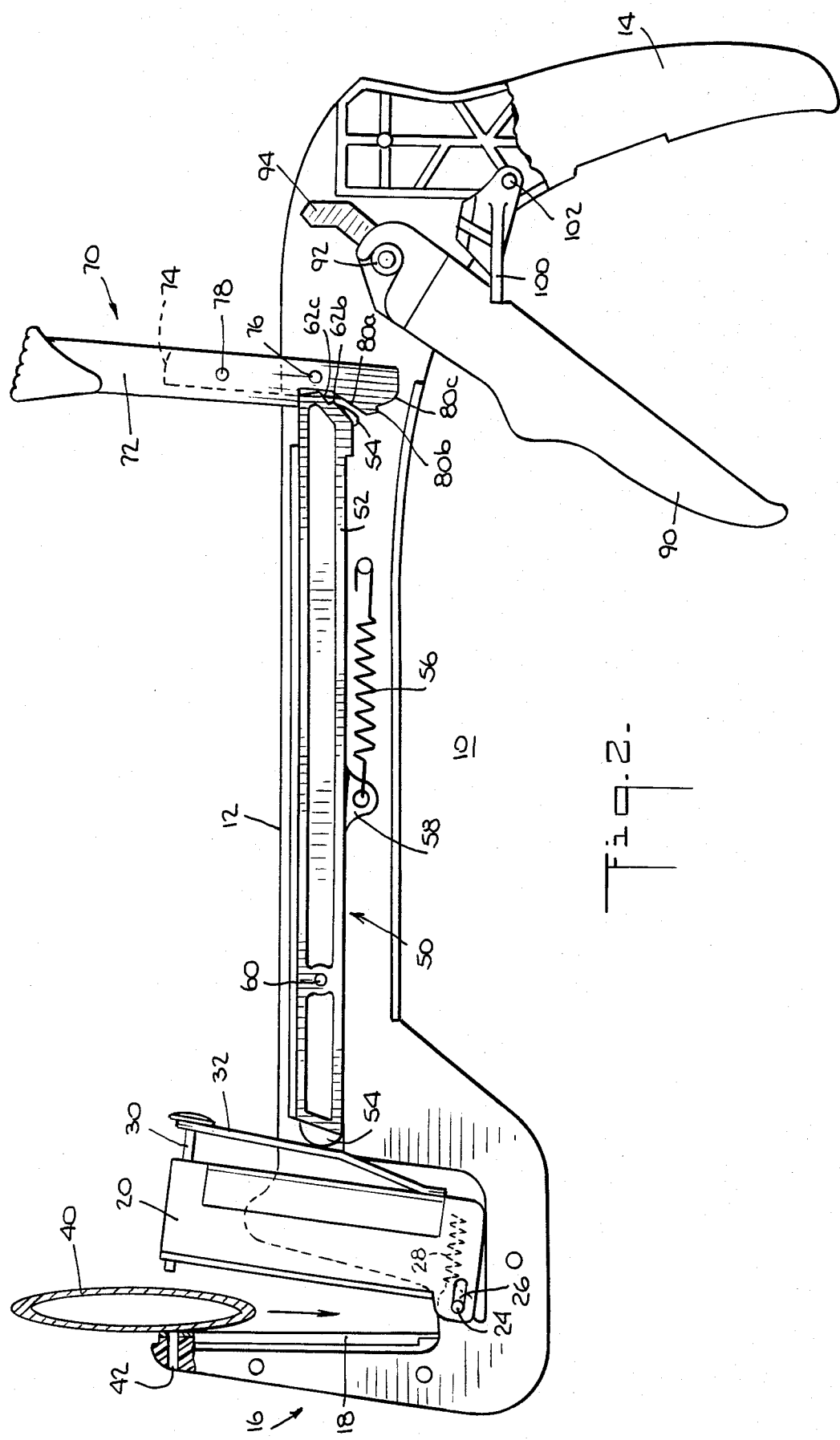
FIG. 2 is a longitudinal sectional view of the apparatus of FIG. 1.

The connection between fastener holding assembly 20 and the remainder of the apparatus is adjacent the lower end of assembly 20 as viewed in FIG. 2. This connection comprises pin 24, the ends of which extend into slots 26 in fastener holding assembly 20. Although basically a pivotal connection, slots 26 are elongated parallel to the longitudinal axis of shaft 12 to allow some linear translation of fastener holding assembly 20 relative to anvil 18. Prestressed compression coil spring 28 is disposed between anvil assembly 18 and fastener holding assembly 20 to resiliently bias these elements apart as shown, for example, in FIGS. 1 and 2. The line of action of spring 28 is above pin 24 as viewed in FIG. 2 so that spring 28 also tends to pivot the upper part of fastener holding assembly 20 away from the adjacent part of anvil 18.

Fastener holding assembly 20 also carries pin 30 near the end of assembly 20 remote from slots 26. Pin 30 is substantially parallel to the longitudinal axis of shaft 12 and is mounted in assembly 20 for reciprocal motion parallel to the longitudinal axis of pin 30. The proximal end of pin 30 is captured by the upper end of leaf spring 32. The lower end of leaf spring 32 is connected to fastener holding assembly 20. Spring 32 resiliently biases pin 30 in the proximal direction as shown, for example, in FIGS. 1 and 2 so that the distal end of pin 30 does not initially project beyond the distal side of fastener holding assembly 20.

Inside shaft 12 is pusher assembly 50 which is mounted for reciprocal motion parallel to the longitudinal axis of shaft 12. Pusher assembly 50 includes two main components: clamp pusher 52 and fastener pusher 54. Fastener pusher 54 is mounted within clamp pusher 52 for longitudinal reciprocal motion relative to pusher 54 and parallel to the longitudinal axis of shaft 12. Both components of pusher assembly 50 are resiliently biased in the proximal direction by prestressed tension coil spring 56 which is connected between shaft 12 and lug 58 projecting down from fastener pusher 54. The return spring force exerted by spring 56 is coupled to clamp pusher 52 by pin 60, which is carried by clamp pusher 52 and extends through an elongated slot (shown in broken lines in FIG. 7) in fastener pusher 54. The distal end of this slot initially abuts pin 60 so that fastener pusher 54 can only move distally relative to clamp pusher 52 from the positions of these elements shown in FIG. 2. In the initial condition of the instrument, the distal end of pusher assembly 50 is spaced from the proximal side of fastener holding assembly 20.

Adjacent the proximal end of pusher assembly 50 is clamp actuator assembly 70. This assembly has two main components: clamp actuator lever 72 and fastener pusher coupler 74. Clamp actuator assembly 70 is pivotally connected to shaft 12 by means of pivot pin 76. Coupler 74 is mounted inside lever 72 for reciprocal motion parallel to the longitudinal axis of lever 72. This mounting includes pins 76 and 78 extending through an elongated slot (shown in broken lines in FIG. 7) in coupler 74.

As mentioned above, pusher assembly 50 is resiliently urged in the proximal direction by return spring 56. As described in more detail below, throughout most of the pivotal motion of clamp actuator 70, a portion of the proximal end of pusher assembly 50 contacts a portion of clamp actuator assembly 70, below pivot pin 76 as viewed in FIG. 2. Accordingly, throughout most of the pivotal motion of clamp actuator assembly 70, that assembly is resiliently urged to pivot counter-clockwise about pin 76 as viewed in FIG. 2 by spring 56 acting through pusher assembly 50.

Handle 90 is pivotally mounted on shaft 12 on the proximal side of clamp actuator assembly 70. The pivotal axis of handle 90 is pin 92, and handle 90 is resiliently biased to pivot clockwise about pin 92 by a coil spring (not shown) concentric with pin 92. Handle 90 is initially latched in its clockwise-most position by safety latch 100, which is pivotally connected to handle 14 by pin 102.

Considering now the operating sequence of the apparatus, the initial condition of the instrument is shown in FIGS. 1–3. When the instrument is to be used, the tissue 40 to be fastened is placed in the instrument between anvil 18 and fastener holding assembly 20. Clamp actuator assembly 70 is then pivoted down to the intermediate position shown in FIGS. 4 and 6. During this phase of the motion of clamp actuator assembly 70, cam surface portion 80a on the distal end of clamp actuator lever 72 contacts cam follower surface portion 62a on the proximal end of clamp pusher 52 and thereby drives pusher assembly 50 in the distal direction. The distal end of fastener pusher 54 passes through a vertical slot (not shown) in leaf spring 32, but the distal end of clamp pusher 52 contacts leaf spring 32 and urges it toward the proximal side of fastener holding assembly 20. This causes the distal end of pin 30 to begin to extend from the distal side of fastener holding assembly 20. It also causes fastener holding assembly 20 to begin to pivot about pin 24 toward anvil assembly 18. Spring 28 is preferably strong enough to keep pin 24 adjacent the distal end of slots 26 during this phase of the motion of fastener holding assembly 20.

At about the time that the portion of the distal side of fastener holding assembly 20 remote from pin 24 contacts anvil assembly 18, cam surface portion 80b contacts cam follower surface portion 62b. Cam surface portion 80b is part of a protrusion from the remainder of cam surface 80a, 80c. Cam follower surface portion 62b is a complementary recess in the remainder of cam follower surface 62a, 62c. Cam surface portion 80b and cam follower surface portion 62b are angled relative to the remaining cam and cam follower surfaces so that they act as a detent or releasable latch. In particular, once clamp actuator assembly 70 has been pivoted far enough for cam and cam follower surface portions 80b and 62b to contact one another, these surface portions cooperate to resist return pivoting of clamp actuator assembly 70. Return spring 56 urges pusher assembly 50 in the proximal direction at all times, but the force of spring 56 is not great enough to overcome the detent action of cooperating surface portions 80b and 62b. Accordingly, after surface portions 80b and 62b have contacted one another, the operator can remove all manual pivoting pressure from clamp actuator assembly 70 and the apparatus will remain in the condition shown in FIGS. 4 and 6 because of the latching effect of surface portions 80b and 62b. This condition of the apparatus is therefore sometimes referred to herein as the intermediate latching condition or position.

Figure 6:
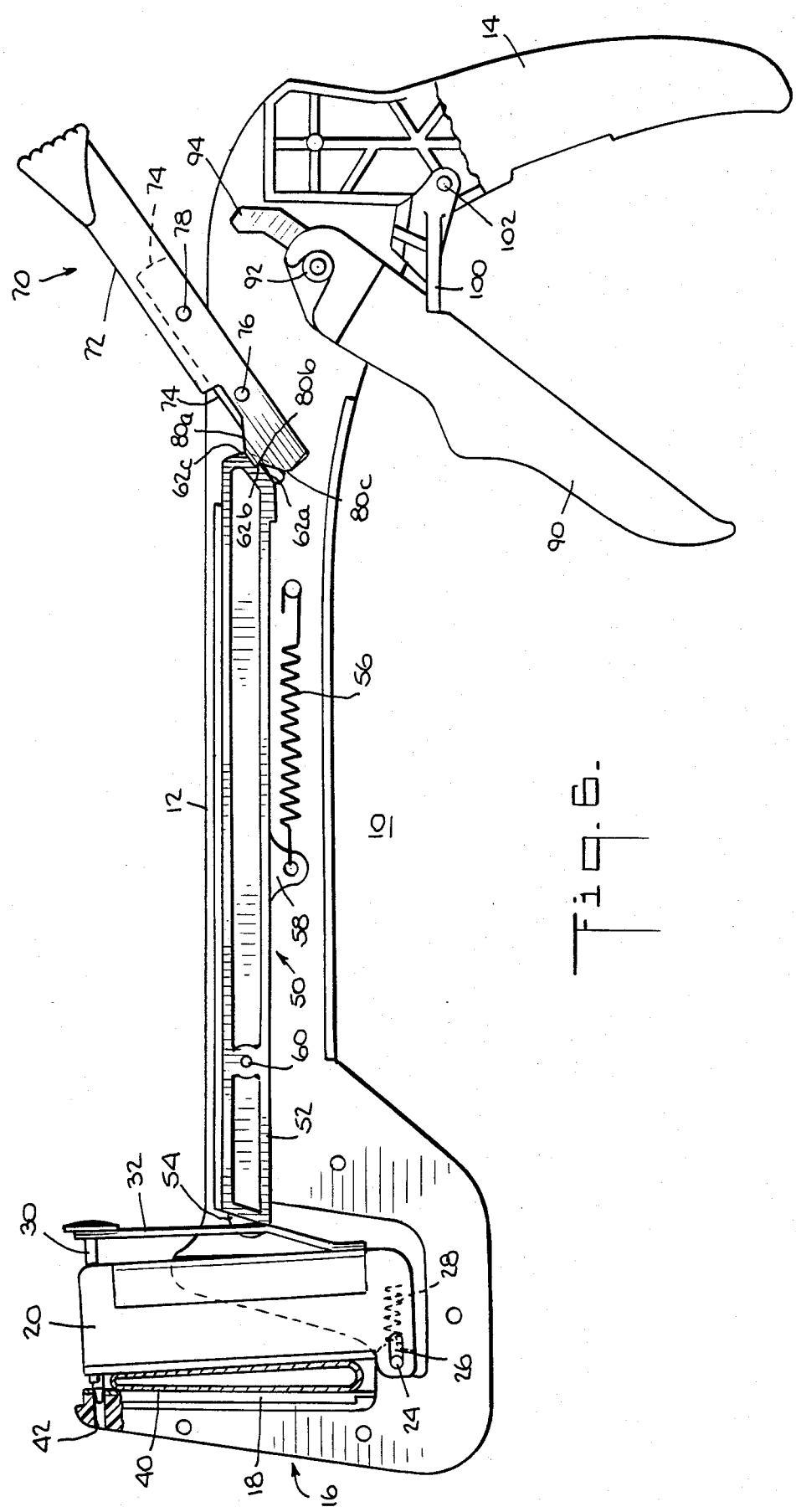
FIG. 6 is a view similar to FIG. 2 showing the apparatus in the operating condition depicted in FIG. 4.

As can be seen in FIG. 6, when the apparatus is in the intermediate latching condition, the tissue 40 to be fastened is completely enclosed within surgical fastener applying assembly 16. The part of fastener holding assembly 20 which is remote from pin 24 is touching or very nearly touching anvil assembly 18, and the distal end of pin 30 has extended from fastener holding assembly 20 and has begun to enter aperture 42 in anvil assembly 18. However, full clamping pressure has not yet been applied to the tissue. Accordingly, if any adjustment must be made to the location of the instrument relative to the tissue, this can be easily accomplished without reopening the instrument. The tissue cannot escape from the instrument during such adjustment because the tissue is completely enclosed in the instrument as described above.

When the operator of the instrument is satisfied with the arrangement of the tissue in the instrument, the operator resumes pivoting clamp actuator assembly 70 down parallel to shaft 12. During this phase of the motion of assembly 70, cam surface portion 80c operates on cam follower surface portion 62c to drive pusher assembly 50 farther in the distal direction. This applies additional force to spring 32, which causes fastener holding assembly 20 to move closer to anvil assembly 18. Spring 28 compresses, and pin 24 moves toward the proximal end of slots 26. Pin 30 extends farther into aperture 42.

When clamp actuator assembly 70 is fully pivoted parallel to shaft 12 as shown in FIGS. 5, 7, and 8, the proximal end of assembly 70 comes to rest against an interior portion of handle 14. Clamp actuator assembly 70 releasably latches in this position because the point of contact between surface portions 80c and 62c is above a horizontal line passing through pin 76 parallel to shaft 12 as viewed in FIG. 7. Handle insert 94 enters a slot in clamp actuator 70 adjacent the proximal end of fastener pusher coupler 74. Pin 24 is adjacent the proximal end of slots 26. Fastener holding assembly 20 is substantially parallel to anvil assembly 18, and the tissue 40 is clamped between those assemblies. The instrument is now ready to apply the fasteners to the tissue.

Figure 9:
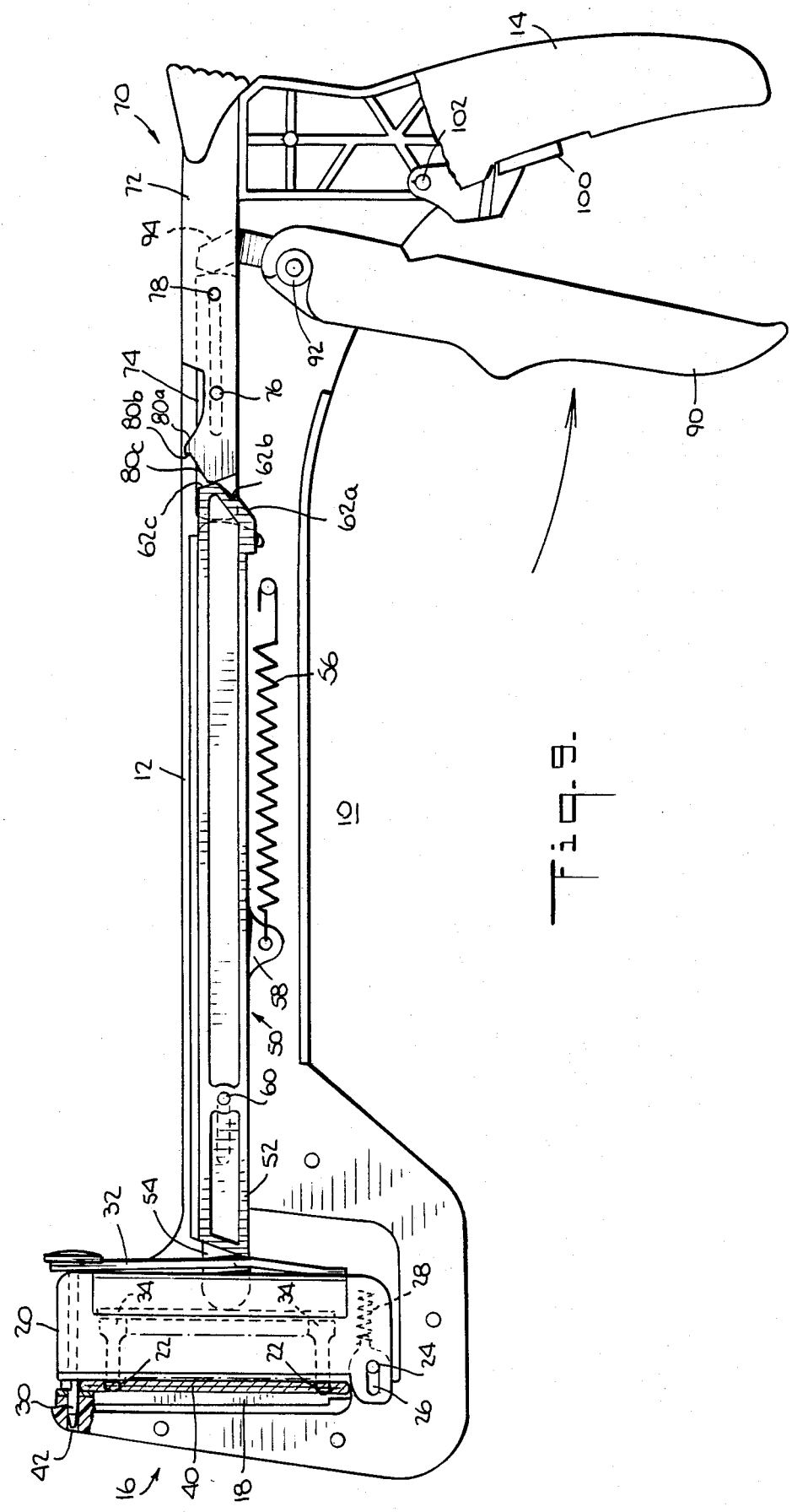
FIG. 9 is a view similar to FIG. 7 showing the apparatus at still another stage in its operating cycle.

To apply the fasteners, safety latch 100 is pivoted down as shown in FIG. 9, and handle 90 is pivoted toward handle 14. This causes handle insert 94 to drive fastener pusher coupler 74 in the distal direction. The distal end of fastener pusher coupler 74 contacts fastener pusher 54 and drives it in the distal direction. The distal end of fastener pusher 54 enters a slot in the proximal side of fastener holding assembly 20 and drives a plurality of individual fastener pushers 34 in the distal direction. Each individual fastener pusher 34 pushes an associated staple 22 from fastener holding assembly 20. The legs of each staple pass through the tissue and are clinched by anvil assembly 18 to fasten the tissue.

To remove the fastened tissue from the instrument, the operator first releases handle 90. Return spring 56 retracts pusher 54 and pusher coupler 74 and restores handle 90 to its initial condition. Then the operator presses up on the proximal end of clamp actuator assembly 70 to overcome the return spring force which latches that assembly down during application of the fasteners as described above. After the latching force has been overcome, return spring 56 retracts pusher assembly 50 and also pivots clamp actuator assembly 70 counter-clockwise as viewed in any of FIGS. 1, 2, 6, 7, or 9. Clamp actuator assembly 70 may or may not stop at the intermediate latching position provided by cam surface portion 80b and cam follower surface portion 62b. If assembly 70 does stop at that position, it will continue moving with the addition of a small amount of manual force. At the end of the return stroke of the instrument, clamp actuator assembly 70, pusher assembly 50, and fastener holding assembly 20 are all in their initial positions shown, for example, in FIGS. 1 and 2. The fastened tissue can then be removed from the instrument.

It will be understood that the embodiment described above is merely illustrative of the principles of the invention and that various modifications can be implemented by those skilled in the art without departing from the scope and spirit of the invention. For example, as has been mentioned, two-part surgical fasteners of the type shown in Noiles U.S. Pat. No. 4,060,089 can be substituted for the metal staples employed in the abovedescribed embodiment.

I claim:

1. Apparatus for applying surgical fasteners to body tissue comprising:
   an anvil assembly;
   a fastener holding assembly movably mounted relative to the anvil assembly; and
   actuator means for supporting the anvil assembly and for moving the fastener holding assembly toward the anvil assembly to clamp the tissue to be fastened between the anvil assembly and the fastener holding assembly, the actuator means including (1) a lever member pivotable by the operator of the apparatus to produce the mechanical work necessary to cause the fastener holding assembly to move and clamp the tissue, the lever member having a cam surface which moves when the lever member is pivoted, and (2) a movable cam follower member having a cam follower surface in contact with the cam surface for transmitting the mechanical work of the lever member from the cam surface to the fastener holding assembly to cause the fastener holding assembly to move and clamp the tissue, the cam surface and the cam follower surface including cooperating segments which comprise detent means for releasably holding the fastener holding assembly at a predetermined position intermediate the position in which the actuator means begins to move the fastener holding assembly toward the anvil assembly and the position in which the tissue is clamped.

2. The apparatus defined in claim 1 wherein the cam follower member translates linearly in response to pivoting of the actuator member.

3. The apparatus defined in claim 1 wherein the anvil assembly and the fastener holding assembly are both longitudinal, and wherein the longitudinal axes of the anvil assembly and the fastener holding assembly are coplanar at all times during operation of the actuator means.

4. The apparatus defined in claim 3 wherein the fastener holding assembly is pivotally mounted adjacent one end of each of the fastener holding and anvil assemblies, and wherein the fastener holding assembly includes means adjacent the end of the fastener holding assembly remote from the pivotal mounting for contacting the anvil assembly adjacent the end of the anvil assembly remote from the pivotal mounting when the fastener holding assembly has pivoted toward the anvil assembly to a predetermined degree.

5. The apparatus defined in claim 4 wherein the detent means becomes operative after the means for contacting the anvil assembly has contacted the anvil assembly.

6. Apparatus for applying surgical fasteners to body tissue comprising:
   a longitudinal anvil assembly;
   a longitudinal fastener holding assembly movably mounted relative to the anvil assembly so that the longitudinal axes of the anvil and the fastener holding assemblies are coplanar; and actuator means for supporting the anvil assembly and for moving the fastener holding assembly toward the anvil assembly to clamp the tissue to be fastened between the anvil assembly and the fastener holding assembly, the actuator means including (1) a lever member pivotally mounted on a fulcrum, the end portion of the lever on one side of the fulcrum being engagable by the operator of the apparatus to pivot the lever and thereby produce the mechanical work required to cause the fastener holding assembly to move and clamp the tissue, the end portion of the lever member on the other side of the fulcrum having a cam surface which moves when the lever member is pivoted, and (2) a movable cam follower member having a cam follower surface in contact with the cam surface for transmitting the mechanical work of the lever member from the cam surface to the fastener holding assembly to cause the fastener holding assembly to move and clamp the tissue, the cam surface and the cam follower surface including cooperating segments which comprise detent means for releasably holding the fastener holding assembly at a predetermined position intermediate the position in which the actuator means begins to move the fastener holding assembly toward the anvil assembly and the position in which the tissue is clamped.

7. The apparatus defined in claim 6 wherein the cooperating segments of the cam and cam follower surface portions comprise a protruberance on one of the cam and cam follower surface portions and a recess in the other of the cam and cam follower surface portions for releasably receiving the protruberance.

8. The apparatus defined in claim 7 wherein the fastener holding assembly is pivotally mounted relative to the anvil assembly adjacent a first end of each of the fastener holding and anvil assemblies.

9. The apparatus defined in claim 8 wherein the fastener holding assembly includes means adjacent the second end of the fastener holding assembly for bridging the gap between the second ends of the fastener holding and anvil assemblies as the fastener holding assembly moves toward the anvil assembly but before the tissue is clamped.

10. The apparatus defined in claim 9 wherein the position at which the detent means releasably holds the fastener holding assembly is intermediate the position at which the bridging means is first effective to bridge the gap between the fastener holding assembly and the anvil assembly and the position at which the tissue is clamped.

11. The apparatus defined in claim 10 wherein the pivotal mounting of the fastener holding assembly includes means for allowing limited linear translation of the fastener holding assembly along an axis substantially perpendicular to the longitudinal axis of the anvil assembly and coplanar with the longitudinal axis of the fastener holding assembly, and wherein the actuator means tends first to pivot the staple holding assembly toward the anvil assembly and to thereafter linearly translate the fastener holding assembly toward the anvil assembly, and wherein the position at which the detent means releasably holds the fastener holding assembly substantially coincides with the transition from pivotal to translational motion of the fastener holding assembly.

12. The apparatus defined in claim 6 further comprising:

return spring means for normally tending to return the apparatus to its initial unactuated condition, the detent means being operative when engaged to prevent the apparatus from returning to the unactuated condition unless additional return force is applied to the apparatus by the operator.

13. The apparatus defined in claim 12 further comprising:

means for releasably latching the fastener holding assembly in the position at which the tissue is clamped.

* * * * *